US012207878B2

United States Patent
Wei et al.

(10) Patent No.: US 12,207,878 B2
(45) Date of Patent: Jan. 28, 2025

(54) APPARATUS AND METHODS FOR THREE DIMENSIONAL OPTICAL IMAGING OF DYNAMICS WITH REDUCED MOTION ARTIFACTS

(71) Applicant: LighTopTech Corp., West Henrietta, NY (US)

(72) Inventors: Wei Wei, Buffalo, NY (US); Cristina Canavesi, West Henrietta, NY (US); Andrea Cogliati, West Henrietta, NY (US)

(73) Assignee: LighTopTech Corp., West Henrietta, NY (US)

( * ) Notice: Subject to any disclaimer, the term of this patent is extended or adjusted under 35 U.S.C. 154(b) by 1167 days.

(21) Appl. No.: 16/985,824

(22) Filed: Aug. 5, 2020

(65) Prior Publication Data

US 2022/0039651 A1 Feb. 10, 2022

(51) Int. Cl.
*A61B 3/12* (2006.01)
*A61B 3/00* (2006.01)
(Continued)

(52) U.S. Cl.
CPC .......... *A61B 3/1233* (2013.01); *A61B 3/0025* (2013.01); *A61B 3/102* (2013.01); *A61B 5/0066* (2013.01)

(58) Field of Classification Search
None
See application file for complete search history.

(56) References Cited

U.S. PATENT DOCUMENTS 7,995,814 B2 8/2011 Fingler et al.
8,180,134 B2 5/2012 Wang
(Continued)

FOREIGN PATENT DOCUMENTS

WO 2014040070 A1 3/2014

OTHER PUBLICATIONS

Yousefi et al" "Eigen Decomposition-Based Clutter Filtering Technique for Optical Microangiography , (Year: 2011).*
(Continued)

*Primary Examiner* — Patrick Fernandes
*Assistant Examiner* — Marjan Saboktakin
(74) *Attorney, Agent, or Firm* — Brian B. Shaw, Esq.; Jodi A. Reynolds, Esq.; Harter Secrest & Emery LLP

(57) ABSTRACT

The present system employs optical coherence tomography (OCT) or optical coherence microscopy (OCM) systems, including ultra-high resolution Gabor-domain optical coherence microscopy (GD-OCM), into a 3D flow imaging technique. This technique models the repeated scans as Gaussian latent variables, with the common variance representing both static tissue structure and dynamic blood flow, and the anisotropic unique variance representing tissue motion in specific frames. Since the motion generated variance is independent from that of the structure or the flow, by iteratively maximizing the combined log-likelihood probability of these two variances modeled through exploratory factor analysis, the unique variance (or the tissue motion) may be largely excluded. In the common variance, the dynamic blood flow may be separated from the static tissue structure, by integrating the factors that represent the relatively low levels of correlation. Compared to a direct differentiation of OCT or OCM scans, the present flow imaging algorithm improves the visualization of capillaries with reduced motion artifacts.

22 Claims, 10 Drawing Sheets

(51) Int. Cl.
*A61B 3/10* (2006.01)
*A61B 5/00* (2006.01)

(56) References Cited

U.S. PATENT DOCUMENTS

| | | |
|---|---|---|
| 8,340,455 B2 | 12/2012 | Rolland et al. |
| 8,750,586 B2 | 6/2014 | Wang et al. |
| 8,823,790 B2 | 9/2014 | Dunn et al. |
| 9,384,404 B2 | 7/2016 | Chen et al. |
| 2014/0073915 A1 | 3/2014 | Lee et al. |
| 2016/0066798 A1 | 3/2016 | Wang et al. |
| 2016/0238370 A1 | 8/2016 | Alexandrov et al. |
| 2018/0242862 A1 | 8/2018 | Jia et al. |
| 2019/0213738 A1* | 7/2019 | Wang .................. G06T 5/50 |
| 2019/0244680 A1* | 8/2019 | Rolfe .................. G06N 3/045 |

OTHER PUBLICATIONS

An et al. (2010) "Ultrahigh sensitive optical microangiography for in vivo imaging of microcirculations within human skin tissue beds," Opt. Express 18(8): 8220-8228.

De Carlo et al. (2015) "A review of optical coherence tomography angiography (OCTA)," International Journal of Retina and Vitreous 1(5): 1-15.

DUNN (2001) "Dynamic Imaging of Cerebral Blood Flow Using Laser Speckle," Cereb. Blood Flow Metab. 21(3): 195-201.

Enfield et al. (2011) "In vivo imaging of the microcirculation of the volar forearm using correlation mapping optical coherence tomography (cmOCT)," Biomed. Opt. Express. 2(5): 1184-1193.

Fingler et al. (2007) "Mobility and transverse flow visualization using phase variance contrast with spectral domain optical coherence tomography," Opt. Express. 15(20): 12636-12653.

Jia et al. (2012) "Split-spectrum amplitude-decorrelation angiography with optical coherence tomography," Optics Express 20(4): 4710-4725.

Shi et al. (2013) "Wide velocity range Doppler optical microangiography using optimized step-scanning protocol with phase variance mask," J. Biomed. Opt. 18(10): 106015-1-106015-4.

Srinivasan et al. (2010) "Rapid volumetric angiography of cortical microvasculature with optical coherence tomography," Opt. Lett. 35(1): 43-45.

Wang et al. (2007) "Three dimensional optical angiography," Opt. Express. 15(7): 4083-4097.

Yousefi et al. (2011) "Eigendecomposition-Based Clutter Filtering Technique for Optical Microangiography," IEEE Trans. Biomed. Eng. 58(8): 2316-2323.

Yu et al. (2010) "Doppler variance imaging for three-dimensional retina and choroid angiography," Biomed. Opt. 15(1): 016029-1-016029-4.

* cited by examiner

| Retina layer | Local variation ||
|---|---|---|
| | DSV | URFA |
| Outer retinal layer | 10.28% | 6.99% |
| Middle retinal layer | 8.40% | 4.41% |
| Inner retinal layer | 3.90% | 2.69% |

APPARATUS AND METHODS FOR THREE DIMENSIONAL OPTICAL IMAGING OF DYNAMICS WITH REDUCED MOTION ARTIFACTS

CROSS-REFERENCE TO RELATED APPLICATIONS

None.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

STATEMENT REGARDING PRIOR DISCLOSURES BY THE INVENTOR OR A JOINT INVENTOR

Not applicable.

BACKGROUND OF THE INVENTION

Field of the Invention

The present disclosure is generally related to the field of optical coherence tomography (OCT), and more particularly to optical coherence tomography angiography (OCTA) and specifically to an apparatus and method of OCTA, including an imaging system, a scanning protocol, and a processing algorithm.

Description of the Related Art

Apart from the anatomic structure, the blood vessels in the micro-circulatory tissue bed support crucial functions in tissue metabolism by exchanging nutrients and oxygen with proximal cells.

Prior visualization technologies have been used to study a number of pathological disorders such as glaucoma, macular degeneration, diabetic retinopathy, dermatitis, melanoma, ischemic stroke and Alzheimer's disease. To better understand disease pathogenesis, there is a current particular interest in the study of how the blood vessels, especially capillaries, interact with the surrounding functional cells.

Prior work in OCT and OCTA has involved the investigation of a number of pathological disorders in the eye and skin, such as glaucoma, macular degeneration, diabetic retinopathy, dermatitis, melanoma, and basal cell carcinomas. However, due to insufficient lateral resolution, the conventional configurations of OCT/OCTA systems have been restricted to imaging of tissue anatomy and vasculature in a relatively macroscopic scale (at the tissue level). To better understand disease pathogenesis, there is a particular interest in the microscopic imaging of both individual cells and capillaries, and accordingly in studying how the microcirculation system interacts with the surrounding functional cells. Further investigations in this field may be of great benefit for state-of-the-art research in biomedicine such as targeted drug delivery or stem cell-based therapies.

For example, the blood-retinal barrier in the eye is composed of tight junctions that are regulated by both endothelial cells in retinal blood vessels and surrounding retina cells (especially neuronal cells or glial cells). This barrier has two-sided functions: on the one hand, it protects the neural retina from the leakage of toxic components and large molecules in blood circulation (especially from the choriocapillaris); on the other hand, it prevents the intravenous injection of drugs from reaching the neural retina. In patients with diabetic retinopathy, the breakdown of the blood-retinal barrier leads to hyperpermeability, resulting in microvascular leakage. Non-invasive visualization of the retina cells and the co-registered capillaries in the blood-retinal barrier region in vivo, in both normal cases and diabetic patients, with a clinically acceptable imaging speed, may help in understanding the cellular mechanisms of blood-retinal barrier dysfunctions, and accordingly developing optimized strategies for the drug delivery.

However, challenges exist in the in vivo imaging of capillaries, mainly due to the artifacts from respiratory, cardiac, or involuntary tissue motion. Such motion artifacts appear as de-correlated noisy background overlaid on the low-flow perfused capillaries, which renders the differentiation of dynamic flow difficult. This is particularly the case for vascular imaging at a high resolution because of two main reasons. First, the small spot size and the short Rayleigh distance of a high-resolution system make it very sensitive to tissue motion in all three-dimensional (3D) directions. Second, 3D high resolution imaging requires large amounts of dense samples, which dramatically increases the acquisition time and the possibility of involving tissue motion.

There is a need for enhancing imaging techniques based on the principle of low-coherence interferometry, wherein the low coherence properties of broadband light sources, allow for tunable depth positioning of the narrow coherence gate/range within a sample. There is a further need for a system and method for in vivo high-resolution and high-definition optical imaging of blood flow in three dimensions (3D blood flow). Specifically, the need exists for improved visualization of capillaries with reduced motion artifacts thereby providing clearer images indicating flow, especially capillary blood flow, which can add in understanding microcirculation in maintaining tissue integrity under both healthy and disease conditions.

BRIEF SUMMARY OF THE INVENTION

The ability to non-invasively image vascular network in vivo is of critical importance for biomedical diagnosis. In one application, the present technique is a 3D flow imaging technique named ultra-high resolution factor angiography (URFA) and developed to extract the vasculature from the microcirculatory tissue bed. The present technique models repeated optical coherence tomography (OCT) or optical coherence microscopy (OCM) scans as Gaussian latent variables, with the common variance representing both static tissue structure and dynamic blood flow, and the anisotropic unique variance representing tissue motion in specific frames. Since the tissue motion generated (anisotropic unique) variance is independent from that of the static tissue structure or the blood flow, by iteratively maximizing the combined log-likelihood probability of these two modeled variances (the static tissue structure and the dynamic blood flow) through exploratory factor analysis to derive corresponding factors, the unique variance (the tissue motion) may be largely excluded, such as reduced by at least 10%, or 20%, or 30% or 40% or 50% depending on the dataset. Meanwhile, in the common variance, the dynamic blood flow may be separated from the static tissue structure, by integrating the factors that represent relatively low levels of correlation. This factor analysis, as belonging to an unsupervised machine learning method, is used to classify the variances (primarily the common variance) based on the relative levels of correlation, e.g. $1^{st}$ factor in the common variance is mainly contributed by the dominant statistic component with high correlation, wherein the higher the order, the weaker the correlation. An OCT angiography image, such as a cross-sectional image of the blood flow, is generated by summing absolute images corresponding to the dynamic factors. However, it is understood, the present OCTA or the 3D flow imaging technique can be more generally applied to blood flow, flow of intralipid, or flow of other scattering particles (e.g. gold nanoparticles). However, it is understood the present disclosure is applicable to enhancing imaging based on the principle of low-coherence interferometry, wherein the low coherence properties of broadband light sources, allow for tunable depth positioning of the narrow coherence gate/range within a sample. For purposes of the present disclosure and without limiting the scope of the disclosure, the method for enhancing imaging is set forth in terms of imaging a blood flow and particularly in vivo blood flow.

The methods described herein provide improved visualization of capillaries with reduced motion artifacts thereby providing clearer images indicating flow, including capillary blood flow, which can aid in understanding the role of microcirculation in maintaining tissue integrity under both healthy and disease conditions. When compared to a direct differentiation of OCT/OCM signals, the present flow imaging algorithm improves the visualization of capillaries with reduced motion artifacts. In one configuration, the present disclosure uses ultra-high resolution Gabor-domain optical coherence microscopy (GD-OCM) datasets to achieve the imaging of the capillary network, wherein the largely reduced motion artifacts in the angiography processing can contribute to further quantitative analysis of the vasculature pattern.

In one configuration, the present disclosure includes a method of in vivo imaging, wherein the method includes modeling an optical coherence tomography dataset as Gaussian latent variables to differentiate common variances and unique variances in the optical coherence tomography dataset to generate a model; iteratively (i) fitting the model through an exploratory factor analysis and (ii) calculating an objective function as a summation of log-likelihood probabilities of the common variances and the unique variances until a calculated improvement of the fitting is less than a predetermined threshold or until a maximum number of iterations have been performed to generate a fitted model; applying the fitted model to reduce unique variances and isolate dynamic factors from static factors in the common variances; and displaying a cross-sectional OCT angiography image by summing absolute values of images corresponding to the dynamic factors.

A further method of in vivo imaging is provided including the steps of repeatedly scanning a tissue sample perfused by blood flow to generate an optical coherence tomography dataset corresponding to a portion of the tissue; modeling the optical coherence tomography dataset as Gaussian latent variables representing static tissue structure, dynamic blood flow and tissue motion to differentiate the static tissue structure and the dynamic blood flow from the tissue motion; iteratively maximizing a combined log-likelihood probability of the modeled static tissue structure, dynamic blood flow, and tissue motion by exploratory factor analysis to exclude at least a portion of the tissue motion; separating the modeled dynamic blood from the modeled tissue structure by integrating factors representing predetermined levels of correlations; and generating a cross-sectional OCT angiography image, such as a display image of blood flow in the tissue, by summing absolute values of images corresponding to predetermined higher orders of factors, such as a factor order greater than 1 or a factor order greater than 2, or at least higher orders than the static tissue.

The present disclosure also includes an apparatus for imaging, such as but not limited to in vivo imaging, wherein the apparatus includes an optical coherence tomography imager configured to scan at least a portion of a sample, such as but not limited to in vivo tissue and generate an optical coherence tomography dataset. The optical coherence tomography imager includes a data processing engine configured to generate an image of the sample, such as an image of in vivo blood flow, by iteratively (i) fitting the optical coherence tomography dataset as a model of Gaussian latent variables differentiating common variances and unique variances in the optical coherence tomography dataset through an exploratory factor analysis and (ii) calculating an objective function as a summation of log-likelihood probabilities of the common variances and the unique variances until an increase of a calculated objective function is less than a predetermined threshold or until a maximum number of iterations has been reached to generate a fitted model; performing an expectation step of the fitted model to generate a plurality of images according to the inter-scan correlation; and generating a display image by summing the absolute values of the plurality of images.

BRIEF DESCRIPTION OF THE SEVERAL VIEWS OF THE DRAWING(S)

FIG. 8 is a table with quantitative metrics for the comparison of the motion artifacts of FIG. 7 between the present URFA method and DSV.

Figure 10A:
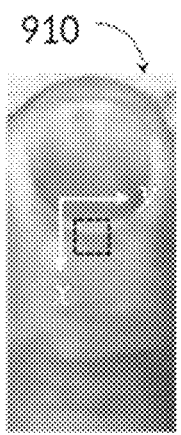

FIG. 10A a top view of a left ring finger of a male adult, with a nailfold region to be imaged as marked by a black square.

Figure 10B:
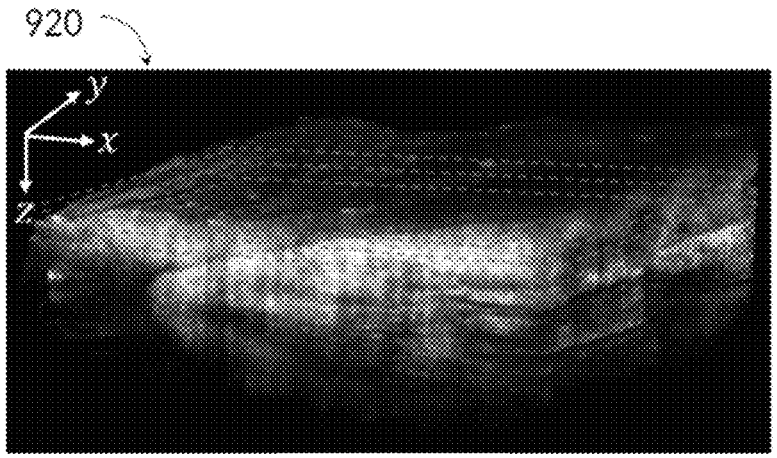

FIG. 10B is a 3D visualization of the scanned nailfold tissue of FIG. 10A according to the present system.

Figure 10C:
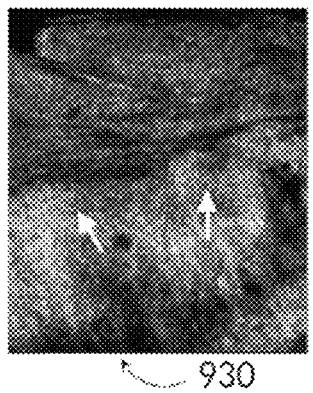

FIG. 10C is a visualization of a first representative cellular structures of FIG. 10B according to the present system.

Figure 10D:

FIG. 10D is a visualization of a second representative cellular structures of FIG. 10B according to the present system.

Figure 10E:
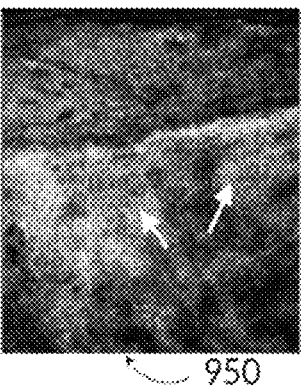

FIG. 10E is a visualization of a third representative cellular structures of FIG. 10B according to the present system.

Figure 10F:
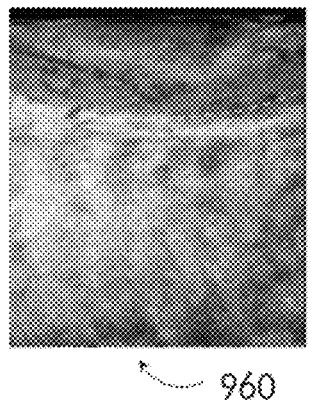

FIG. 10F is an en face view mean intensity projection of the nailfold structure according to the present system, where the boundary between the nail plate and the nailfold soft tissue of FIG. 10A is demarcated by a dashed curve.

Figure 10G:
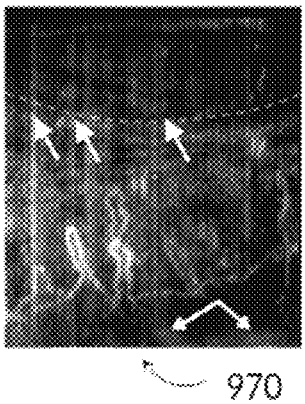

FIG. 10G is an en face view mean intensity projection of the nailfold vasculature obtained with DSV.

Figure 10H:
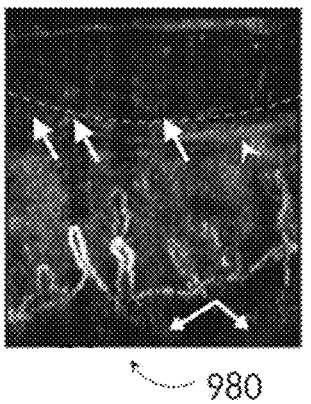

FIG. 10H is an en face view mean intensity projection of the nailfold vasculature obtained according to the present URFA method.

DETAILED DESCRIPTION OF THE INVENTION

In the following detailed description, reference is made to the accompanying figures, which form a part hereof, by a way of illustrative embodiments that can be practically achieved. It is generally understood that other embodiments can be utilized and other logical changes can be made without departing from the scope of concepts described herein. The presented operations, as multiple general discrete operations, can be combined, separated or rearranged in a wide variety of manners, without any dependent in the order.

This disclosure hereby incorporates by reference, in its entirety, U.S. Pat. No. 8,340,455, issuing on Dec. 25, 2012, entitled "Systems and methods for performing Gabor-domain optical coherence microscopy."

In the embodiments herein, images of tissue structure can be obtained using optical coherence tomography (OCT) by Fourier transform of the sequentially captured spectral interference signals. Typically, an OCT scan can be an one dimensional (1D) A-line, corresponding to a depth encoded profile of tissue reflections along the optical axis of an OCT imaging probe (z-direction); or a two dimensional (2D) B-frame, corresponding to a cross-sectional image by laterally aligning a series of A-lines along the fast scanning direction (x-direction); or a three dimensional (3D) volume, corresponding to a series of B-frames aligned along the slow scanning direction (y-direction).

Correspondingly, OCT angiography (OCTA) can be processed with repeated A-lines, B-frames, or even volumes. The time-interval between consecutive scans determines the temporal sensitivity of the present angiography algorithm to the flow speed. In consideration of current OCT system speed, an available OCT scanning protocol is repeating B-frames with an interval of a few to tens of milliseconds. Embodiments herein utilize the present OCTA algorithm, namely ultra-high resolution factor angiography (URFA) to extract and visualize the tissue perfusion down to individual capillaries, and meanwhile model the tissue motion as unique variance in specific scans and accordingly reduce the motion artifacts.

The present method enables high resolution angiography because of its key advantage in motion reduction, which effectively overcomes the challenges in high resolution OCTA due to small spot size, short Rayleigh distance, and long acquisition time. It is generally understood that the present URFA algorithm is equally applicable to datasets from other OCTA systems with less rigorous requirements of image resolution. That is, the present OCTA method, due to its capability of motion reduction, is a good match with ultra-high resolution OCTA.

After OCTA processing, the image of blood vessels can be represented as a cross-sectional B-frame or a 3D volume. A segmentation algorithm may be adopted to segment the 3D volume into multiple layers, and the vasculature pattern in each layer can be visualized from en face view (x-y plane)

through maximum intensity projection or mean intensity projection. It is understood that in the en face view OCTA images, the motion artifacts, as projections of de-correlated noisy background, may appear as bright lines along the fast scanning direction.

Figure 1:
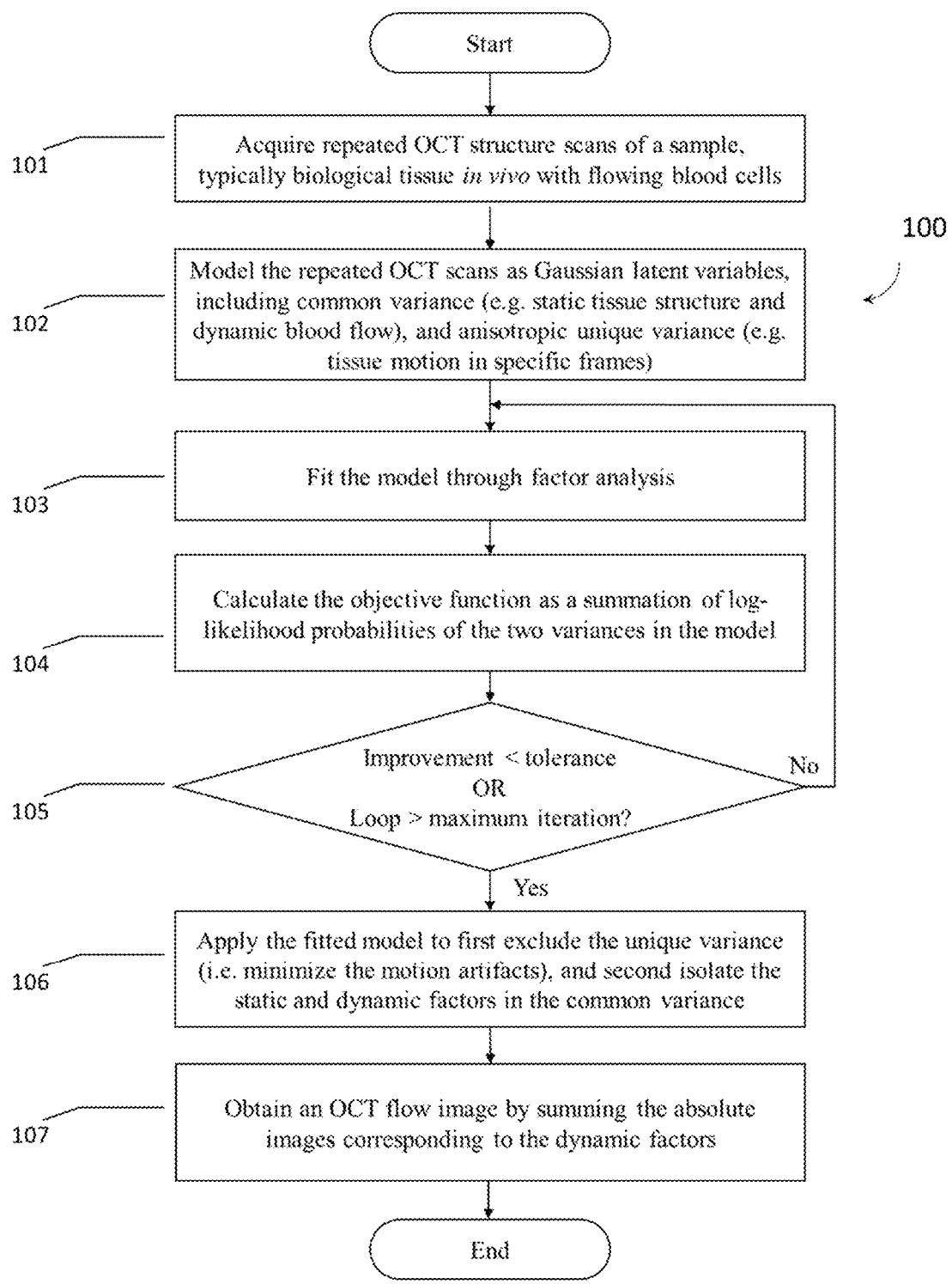
FIG. 1 is a flowchart of the present method for optical imaging of in vivo 3D blood flow with reduced motion artifacts.

FIG. 1 is a flowchart of the URFA method 100 that can be used to image 3D vasculature with reduced motion artifacts, in accordance with the present disclosure. At step 101, the method 100 obtains an OCT dataset, wherein in one configuration the OCT dataset is a plurality of B-frames acquired by repetitively scanning the blood perfused tissue bed, such as of a living subject including but not limited to animals or humans, including skin or eye, including but not limited to finger tissue or retina tissue. However, it is contemplated the present method can be applied to a previously acquired OCT dataset, such as an OCT dataset generated by a third party. Thus, the present method can process previously acquired OCT datasets. Further, as used herein the term OCT encompasses imaging techniques based on the principle of low-coherence interferometry, wherein the low coherence properties of broadband light sources, allow for tunable depth positioning of the narrow coherence gate/range within a sample. Thus, optical coherence microscopy (OCM) as used herein is taken as being a subset of and encompassed by the term OCT.

At step 102, the method 100 models the OCT dataset, such as the repeated B-frames, as Gaussian latent variables, with a common variance representing static tissue structure and blood flow that share similar distributions among frames, and an anisotropic unique variance representing the tissue motion in specific frames. As the common variance (the static tissue structure or the blood flow) and unique variance (the tissue motion) are statistically independent, the method 100 further differentiates these two variances in the model through an iterative processing including steps 103, 104 and 105.

At step 103, the model is fitted through exploratory factor analysis that estimates the representative factor, i.e. the regression coefficients between frames and factors that quantify the influence of a common factor on a scanned frame. At step 104, as an evaluation of fitting accuracy, an objective function is designed with the summation of log-likelihood probabilities of the common variance and the unique variance of the model. At step 105, the robustness of the model fitting is guaranteed by the improvement of the fitting with respect to the last iteration and the maximum number of iterations. By applying the fitted model to transform the acquired dataset at step 106, the unique variance may be separated, corresponding to minimizing the motion induced mismatches in the repeated frames. Meanwhile, the factors derived for the common variance are further subdivided into multiple factors at step 106, depending on the levels of inter-scan correlations. Due to the fast scanning speed of OCT and the hemodynamic nature of blood flow, the first factor is always dominated by the static component. Conversely, at step 107, the dynamic blood flow may be resolved and set forth in a display image, such as a cross-sectional OCT angiograph image, by summing the absolute values of images corresponding to a predetermined order or an order higher than the order of the static tissue. For example, typically the summed values for the orders greater than 1 are used for imaging the retina, whereas orders greater than 2 are used for imaging the skin depending on the scattering property of the tissue.

Figure 2:
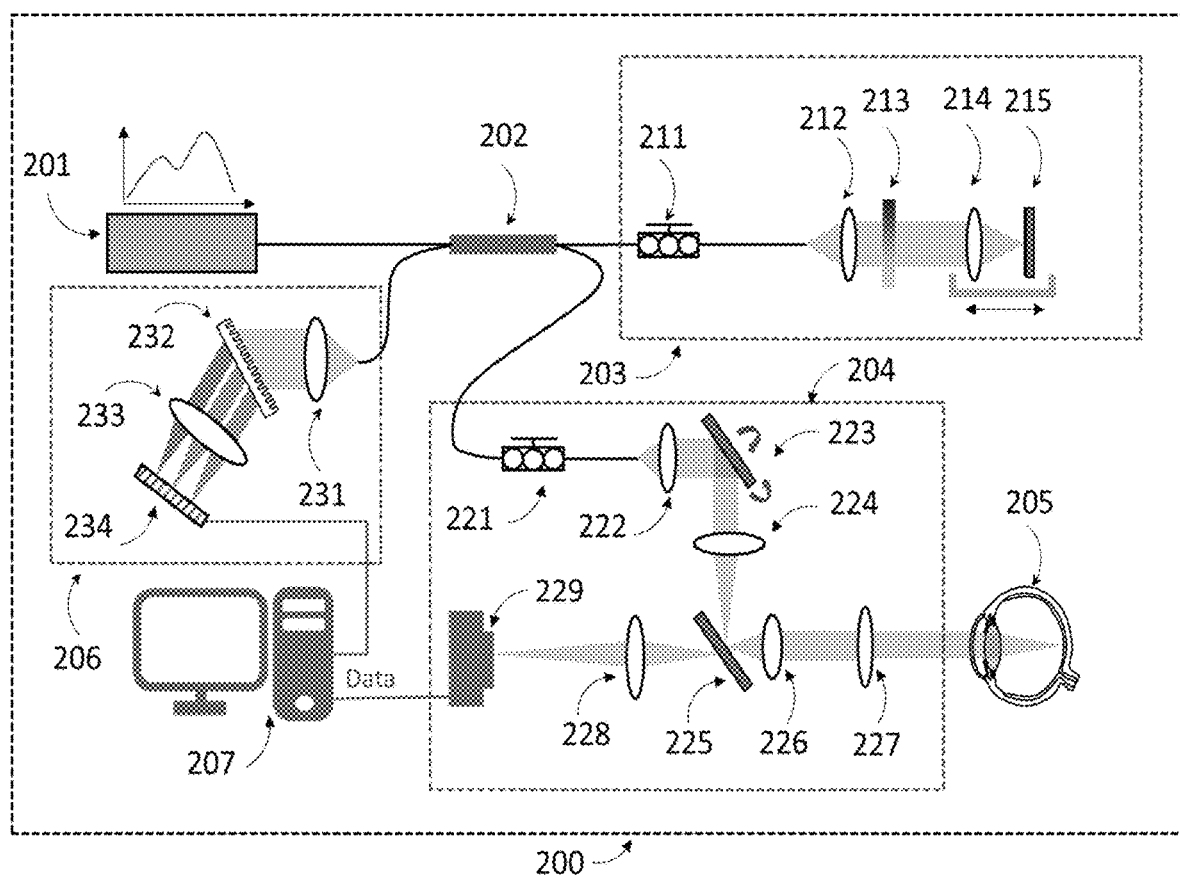
FIG. 2 is a schematic of an exemplary OCT imaging apparatus for the present system.

FIG. 2 is a schematic of an exemplary OCT imager, such as imaging system 200, in accordance with various embodiments. The OCT imager as system 200 is a spectral domain OCT, which includes a light source 201, a coupler 202, a reference arm 203, a sample arm 204 focusing the light beam into a tissue sample 205, such as a rat eye 205, a detection spectrometer 206, and a data processing engine 207. As an example, the light source 201 may be a broadband super luminescent diode with a center wavelength of 840 nm and a bandwidth of 120 nm, corresponding to an axial resolution of 2.6 µm in air. Although the present method is set forth with a spectral domain OCT system, it is understood the present method can be equally applicable to swept source OCT or full field OCT.

Light from the light source 201 is first split by the coupler 202 into two paths. One path is named the reference arm 203, that may include a polarization controller 211, a collimator 212, a variable neutral density filter 213, a re-focusing lens 214, and a reference mirror 215. The reference mirror 215 and the re-focusing lens 214 may be carried on a translational stage for quick adjusting of optical delay. Another path is the sample arm 205, that can include a polarization controller 221, a collimator 222, a 2D scanner pair 223 (that can be Galvo scanners, resonant scanners or micro-electro-mechanical system (MEMS) scanners), two relay lenses 224 and 226, and an objective lens 227. Additionally, a 2D fundus image of the eye may be captured with a dichroic mirror 225, a zoom lens 228, and a fundus camera 229. Light reflected back from the reference arm 203 and the sample arm 205 interfere at the coupler 202, and are then detected by the spectrometer 206, which includes a collimating lens 231, a grating 232, a focusing lens 233, and a fast line-scan camera 234. The detected spectral interference signal and the fundus image are transferred to and post-processed in the data processing engine 207.

The data processing engine 207 is configured to carry out the steps of the flowchart of FIG. 1. Each block in the flowchart can represent a module, a segment, or a portion of program code, which includes one or more instructions executable by a processor for implementing specific logical functions or steps in the process. The program code may be stored on any type of computer readable medium, for example, data storage including a one or more computer-readable storage media that may be read or accessed by the processor, and may be a fixed or removable hard drive, a flash memory, a rewritable optical disk, a rewritable magnetic tape, or some combination of the above. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable medium may also be any other volatile or non-volatile storage system. The computer readable medium may be considered a computer readable storage medium, a tangible storage device, or other article of manufacture, for example. Alternatively, program code, instructions, and/or data structures may be transmitted via a wired or wireless communications network.

Figure 3A:
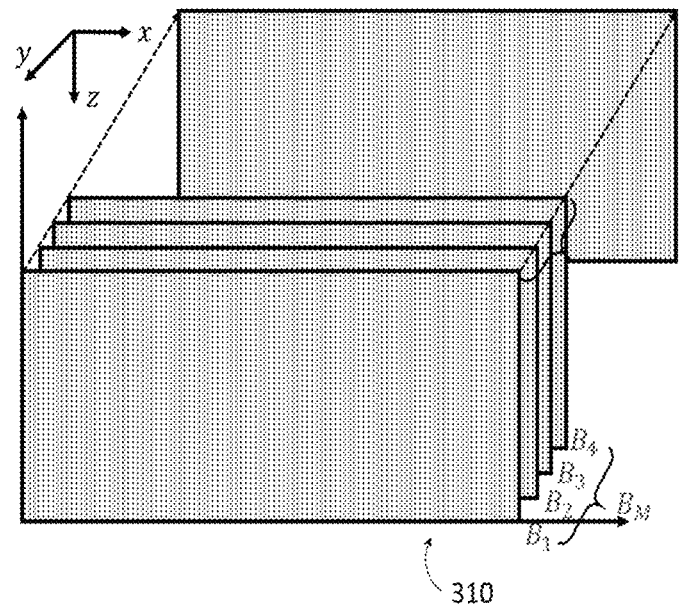
FIG. 3A is a schematic of an exemplary scanning protocol for the present system.

In one exemplary imaging to provide 3D imaging of retinal vasculature of a Brown Norway rat in vivo, the scanning protocol was designed as in FIG. 3A. The scanned 3D OCT dataset consisted of 1,600 B-frames with 400 A-lines in each frame. At one cross-sectional location, the B-frame scanning was repeated 4 times ($B_1$, $B_2$, $B_3$, $B_4$) 310 with a frame rate of about 67 frames per second, resulting in a total acquisition time of 24 seconds. With respect to each location, the repeated B-frames were processed with the present URFA method for visualization of blood flow, and the repeated B-frames were also averaged to enhance the visualization of tissue structure. The lateral sampling of OCT structure and OCTA vasculature were both 400×400, which covered a field of view of 1.4×1.4 mm. The 3D dataset (in this example of a retina) was further flattened and segmented into 3 anatomical layers, as the outer retinal layer (ORL), the middle retinal layer (MRL), and inner retinal layer (IRL).

For a typical 3-year-old Brown Norway rat, the respiratory rate is about 85 breaths per minute, and the heart beat rate is about 400 beats per minutes. Accordingly, a scanned 3D OCT dataset acquisition over a 24 second acquisition time may be affected 34 times by respiratory motion and 160 times by cardiac motion over the acquisition time, as well as affected by additional involutory tremor, micro-saccades, or drift. These types of motion may combine and result in complicated OCTA artifacts, which are difficult, if not impossible to be generalized by a simple isotropic motion model.

Figure 3B:
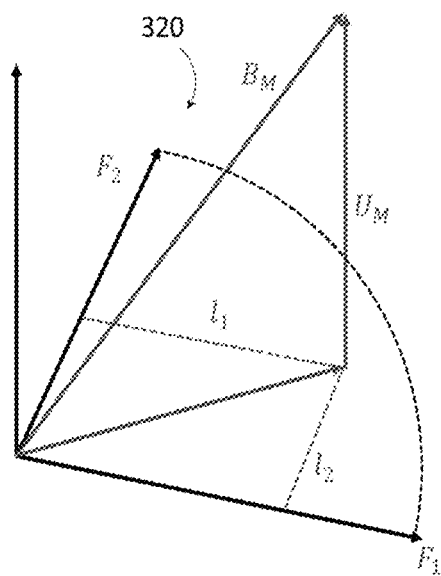
FIG. 3B is a schematic of the factor analysis utilized in the present ultra-high resolution factor angiography (URFA) method.

FIG. 3B depicts the factor analysis of the repeated B-frames utilized in the URFA 320. Initially, the n times repeated (n=4 in this example) B-frames are rearranged as a 2D matrix $B_M = \{B_1, B_2, \ldots B_n\}$, in which each B-frame ($B_i$) is serialized by concatenating the contained A-lines. As a repeated collection of large independent samples of tissue reflections from numerous spatial locations, the $B_M$ follows a multivariate Gaussian random process, which may be further described through a generative latent variable model as:

$$B_M = C + S + \varepsilon \quad (1)$$

where C represents the common variance, meaning that only the variance shared among all B-frames are accounted for; S represents the specific variance, i.e., the unshared variance in specific frames, such as tissue motion; and $\varepsilon$ represents the residual error variance from the measurement, such as detector noise.

In the factor analysis, the specific variance and the residual error variance are modeled jointly, which can be further generalized as an anisotropic unique variance. For a typical Fourier domain OCT system working in the shot noise limited regime, the unique variance is mainly contributed by the specific variance (i.e., tissue motion) as compared to the random error variance (i.e., system noise). On the other hand, the common variance can be calculated as a multiplication between the common factor matrix F and the corresponding factor loadings L. Therefore, the generative latent variable model in equation (1) can be rewritten as:

$$B_M = LF + U_M \quad (2)$$

in which, F represents a matrix of m unobserved latent variables with each row indicating an independent factor $\{f_{i1}, f_{i2}, \ldots f_{iS}\}$; L represents an n×m matrix of the factor loadings with its column vectors $\{l_{1j}, l_{2j}, \ldots l_{nj}\}$ indicating the influence of one factor component on each scanned frame; $U_M$ represents the anisotropic unique variance following a Gaussian distribution. Such latent variable model is named as "generative", because it describes how $B_M$ is generated from F by seeking the linear combinations of the common factors in F.

A matrix expression of equation (2) is expressed as:

$$\begin{bmatrix} b_{11} & b_{12} & \cdots & b_{1j} & b_{1s} \\ b_{21} & b_{22} & \cdots & b_{2j} & b_{2s} \\ \vdots & \vdots & \ddots & \vdots & \vdots \\ b_{i1} & b_{i2} & \cdots & b_{ij} & b_{is} \\ b_{n1} & b_{n2} & \cdots & b_{nj} & b_{ns} \end{bmatrix} = \begin{bmatrix} l_{11} & l_{12} & \cdots & l_{1j} & l_{1m} \\ l_{21} & l_{22} & \cdots & l_{2j} & l_{2m} \\ \vdots & \vdots & \ddots & \vdots & \vdots \\ l_{i1} & l_{i2} & \cdots & l_{ij} & l_{im} \\ l_{n1} & l_{n2} & \cdots & l_{nj} & l_{nm} \end{bmatrix}$$

$$\begin{bmatrix} f_{11} & f_{12} & \cdots & f_{1j} & f_{1s} \\ f_{21} & f_{22} & \cdots & f_{2j} & f_{2s} \\ \vdots & \vdots & \ddots & \vdots & \vdots \\ f_{i1} & f_{i2} & \cdots & f_{ij} & f_{is} \\ f_{m1} & f_{m2} & \cdots & f_{mj} & f_{ms} \end{bmatrix} + \begin{bmatrix} u_{11} & 0 & \cdots & 0 & 0 \\ 0 & u_{22} & \cdots & 0 & 0 \\ \vdots & \vdots & \ddots & \vdots & \vdots \\ 0 & 0 & \cdots & u_{ii} & 0 \\ 0 & 0 & \cdots & 0 & u_{nn} \end{bmatrix} \quad (2)$$

For the matrices herein, s denotes the number of pixel samples in one B-frame; i and j denote the row and the column indices of the matrices, respectively.

In order to identify the factors that produce correlations among the B-frames and extract the blood flow information corresponding to relatively low levels of inter-frame correlations, a covariance matrix $K_{BB}$ is constructed as:

$$K_{BB} = B_M B_M^T = (LF + U_M)(LF + U_M)^T \quad (3)$$

According to the definitions of the common variance and the unique variance, F and $U_M$ are statistically independent. Additionally, in order to separate the static factor and the dynamic factor, without loss of generality, the factor axes are assumed to follow varimax rotation, which means the variance of the squared loadings $\{l_{1j}, l_{2j}, \ldots l_{nj}\}$ of L on all the factors $\{f_{i1}, f_{i2}, \ldots f_{iS}\}$ of F are maximized. Therefore, the factors in F are also independent of each other, i.e., F is an orthogonal matrix. The covariance matrix in equation (3) can be derived as:

$$K_{BB} = LIL^T + \psi = LL^T + \psi \quad (4)$$

where $I = FF^T$ is a m×m identity matrix of the m factors, $\psi = U_M U_M^T$ is the covariance of $U_M$ described as a n×n anisotropic diagonal matrix $\psi = \mathrm{diag}(\psi_{11}, \psi_{22}, \ldots \psi_{nn})$.

A matrix expression of equation (4) is written as:

$$\begin{bmatrix} k_{11} & k_{12} & \cdots & k_{1j} & k_{1n} \\ k_{21} & k_{22} & \cdots & k_{2j} & k_{2n} \\ \vdots & \vdots & \ddots & \vdots & \vdots \\ k_{i1} & k_{i2} & \cdots & k_{ij} & k_{in} \\ k_{n1} & k_{n2} & \cdots & k_{nj} & k_{nn} \end{bmatrix} = \begin{bmatrix} l_{11} & l_{12} & \cdots & l_{1j} & l_{1m} \\ l_{21} & l_{22} & \cdots & l_{2j} & l_{2m} \\ \vdots & \vdots & \ddots & \vdots & \vdots \\ l_{i1} & l_{i2} & \cdots & l_{ij} & l_{im} \\ l_{n1} & l_{n2} & \cdots & l_{nj} & l_{nm} \end{bmatrix}$$

$$\begin{bmatrix} l_{11} & l_{12} & \cdots & l_{i1} & l_{n1} \\ l_{21} & l_{22} & \cdots & l_{i2} & l_{n2} \\ \vdots & \vdots & \ddots & \vdots & \vdots \\ l_{1j} & l_{2j} & \cdots & l_{ij} & l_{nj} \\ l_{1m} & l_{2m} & \cdots & l_{im} & l_{nm} \end{bmatrix} + \begin{bmatrix} \psi_{11} & 0 & \cdots & 0 & 0 \\ 0 & \psi_{22} & \cdots & 0 & 0 \\ \vdots & \vdots & \ddots & \vdots & \vdots \\ 0 & 0 & \cdots & \psi_{ii} & 0 \\ 0 & 0 & \cdots & 0 & \psi_{nn} \end{bmatrix} \quad (5)$$

Rearranging equation (4) as $K_{BB} - \psi = LL^T$, the loading matrix L may be estimated through a principal factor method. First, the off-diagonal elements in $K_{BB} - \psi$ are directly calculated as the B-frame covariances $k_{ij, i \neq j}$. Second, the diagonal elements can be initialized as $$k_{ii} - \frac{1}{k_{ii}},$$

since normally $K_{BB}$ is a non-singular matrix with an existing inverse. Otherwise, the diagonal elements can be replaced by the largest covariance in the i-th row of $K_{BB}$. With the pre-defined $K_{BB} - \psi$, the calculation of L is equivalent to finding the orthogonal matrix of $K_{BB}-\psi$ through singular value decomposition, expressed as:

$$K_{BB}-\psi=LL^T=\Sigma_{i=1}^{m}\lambda_j e_{ij}^2 \quad (6)$$

where the elements in the factor loading L are expressed as $l_{ij}=\sqrt{\lambda_j}e_{ij}$. From another perspective, the diagonal elements of are updated with a better estimation as $\psi_{ii}=k_{ii}-\Sigma_{i=1}^{m}\lambda_j e_{ij}^2$. Therefore, the principal factor method can be iterated to increase the modeling accuracy, with an improved estimation of L and $\psi$ after each iteration.

As an evaluation of the accuracy, an objective function is designed with the summation of log-likelihood probabilities of the common variance and the unique variance as:

$$\text{Objective} = \quad (7)$$
$$\log P(K_{BB} \mid L, \psi) = -\frac{n}{2}\left(\sum_{j=1}^{m}\log(\lambda_j) + \sum_{i=1}^{n}\log(\psi_i) + res + const\right)$$

where $\Sigma_{j=1}^{m}\log(\lambda_j)$ represents the log-likelihood of the common variance, $\Sigma_{i=1}^{n}\log(\psi_i)$ represents the log-likelihood of the unique variance, $res=\Sigma_{j=m+1}^{n}\lambda_j$ accounts for the residual fitting loss in the singular value decomposition, and const is a bias constant term. In the present URFA method, the number of factors (m) is a user-defined input parameter, which is typically set as m=min (n, 5), in consideration of the computation time cost and the capability of resolving blood vessels. In current scenario of OCTA with a small amount of repeated B-frames (n=4), m is equal to the B-frame repeats n, therefore res=0.

The convergence of the modeling is reached at iteration N, if either of the following conditions is satisfied:

(a) the improvement of the fitting is smaller than a pre-defined tolerance a, calculated as:

$$\text{Objective}(N+1)-\text{Objective}(N)<\sigma \quad (8)$$

or (b) the maximum number of iterations is reached, as $N>N_{max}$.

Practically, the tolerance a is set as 0.01, and $N_{max}$ is set as 100. Finally, the optimized L and $\psi$ are the ones obtained from the last iteration. This parallels the maximization step of an expectation-maximization (EM) algorithm, which computes the parameters that maximize the expected log-likelihood.

By additionally performing an expectation step of the EM algorithm with the optimized L and $\psi$, the cross-sectional images of the separated factor components can be calculated as, $$E[F] = \frac{L^T \psi^{-1} B_M}{(I + L^T \psi^{-1} L)^{-1}} \quad (9)$$

where E[F] represents the expectation of the factor matrix F. It is noted that in equation (9), the inversions of matrices are only performed for a relatively small m×m matrix $(1+L^T\psi^{-1}L)$ and a diagonal n×n matrix $(\psi)$, which should be trivial to compute. The rows of E[F] are arranged in the descending order of correlations, with the first few factors (typically 1 or 2) mainly contributed by the static tissue structure of highly correlated signals, and the remaining factors mainly contributed by blood flow of relatively low correlations.

In the present URFA algorithm, the cross-sectional OCTA image is calculated by summing the absolute values of the images corresponding to high order factors (typical order of factors larger than 1 for the retina tissue) as:

$$\text{URFA}=\Sigma_{i=2}^{m}f_{ij} \quad (10)$$

Because the URFA algorithm only considers the factors of the common variance during the reconstruction of blood flow, the unique variance (or the tissue motion) is largely reduced in the resulting OCTA image.

For comparison purpose, another algorithm based on differentiation speckle variance (DSV) that has been widely used in the clinical OCTA is also utilized herein to process the same dataset. The DSV algorithm can be generalized as follows:

$$DSV = \frac{1}{n-1}\sum_{i=1}^{n-1}|B_{l+1} - B_l| \quad (11)$$

where l is the index of the repeated B-frames, $|B_{l+1}-B_l|$ represents the absolute value of a subtraction between adjacent frames.

Figure 4A:
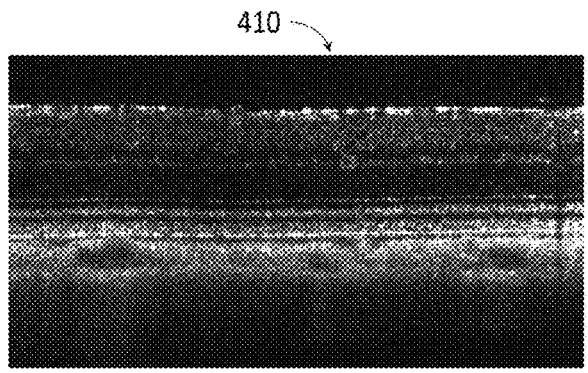
FIG. 4A is a static factor component of the common variance in the repeated OCT cross-sectional scans of a rat retina.
Figure 4B:
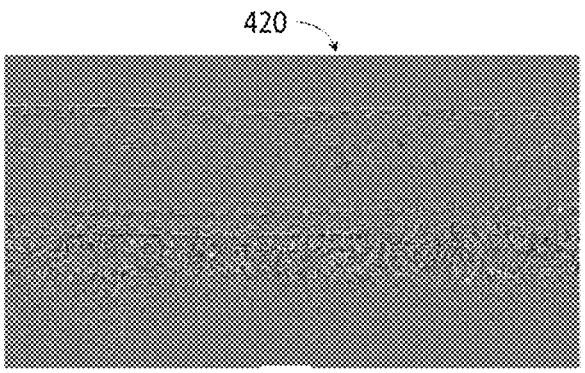
FIG. 4B is a first dynamic factor component of the common variance in the repeated OCT cross-sectional scans of the rat retina of FIG. 4A.
Figure 4C:
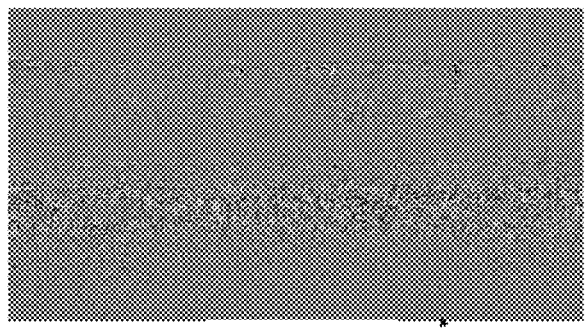
FIG. 4C is a second dynamic factor component of the common variance in the repeated OCT cross-sectional scans of the rat retina of FIG. 4A.
Figure 4D:
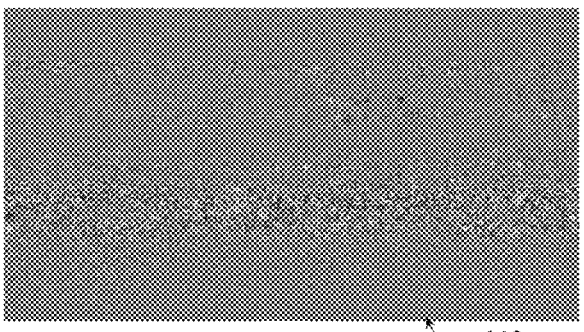
FIG. 4D is a third dynamic factor component of the common variance in the repeated OCT cross-sectional scans of the rat retina of FIG. 4A.
Figure 4E:
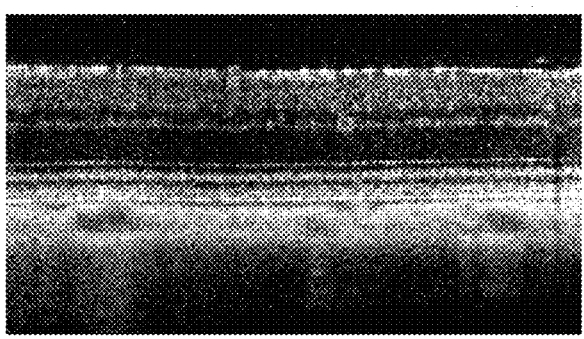
FIG. 4E shows a representative cross-section of frame-averaged tissue structure from the repeated OCT scans of the rat retina of FIG. 4A.
Figure 4F:
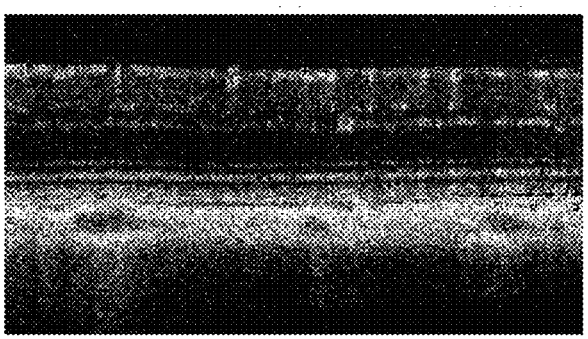
FIG. 4F shows a representative cross-section of dynamic blood flow from the repeated OCT scans of the rat retina of FIG. 4A.

Obtained with the present URFA processing, FIGS. 4A-4D depict four factor components of the common variance from the repeated B-frames of the rat retina, arranged in the descending order of correlations (or how "common" the variances are). FIG. 4A depicts the static factor, which is mainly contributed by the static tissue structure 410. FIGS. 4B-4D depict 3 different dynamic factors that are mainly contributed by the dynamic blood flow 420, 430 and 440, in which the absolution pixel intensities may represent the flow speed, and the bright/dark pixels distinguished from the grayish background may represent the flow moving towards opposite directions. FIG. 4E depicts the log-scale compressed average of the B-frames corresponding to an enhanced visualization of tissue structure 450. FIG. 4F depicts the log-scale compressed summation of the absolute flow components 420, 430 and 440, corresponding to the dynamic blood flow 460.

Figure 5A:
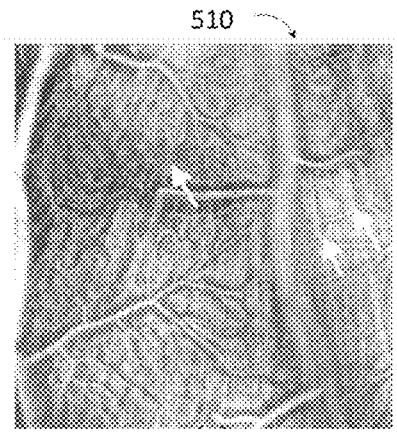
FIG. 5A shows the en face view mean intensity projections of the tissue structure corresponding to the outer retinal layer (ORL) of the rat retina of FIG. 4A.
Figure 5B:
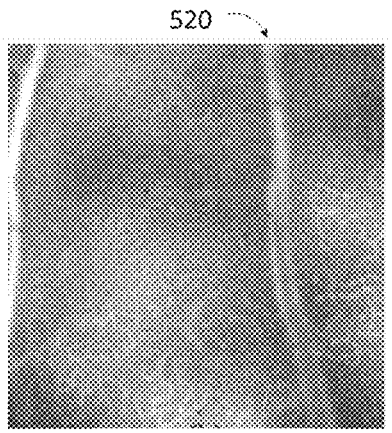
FIG. 5B shows the en face view mean intensity projections of the tissue structure corresponding to the middle retinal layer (MRL) of the rat retina of FIG. 4A.
Figure 5C:
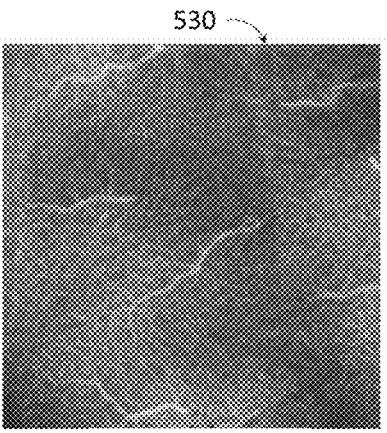
FIG. 5C shows the en face view mean intensity projections of the tissue structure corresponding to the inner retinal layer (IRL) of the rat retina of FIG. 4A.

FIGS. 5A-5C depict the en face view mean intensity projections of the tissue structure, corresponding to ORL 510, MRL 520, and IRL 530, respectively. The nerve fiber bundles in the ORL are visualized as strong back-scattering signals in the OCT structure, as marked by the arrows in 510. While, the blood vessels, as buried in the scattering tissue background, are difficult to be resolved, especially in the MRL 520.

Figure 5D:
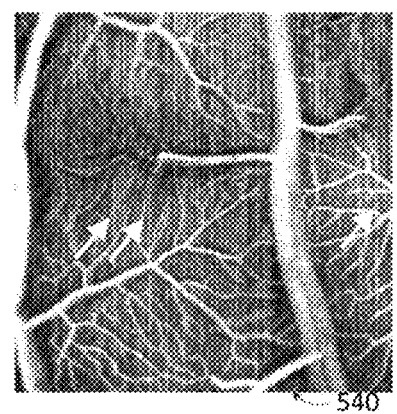
FIG. 5D shows the en face view mean intensity projection of the vasculatures processed with differentiation speckle variance (DSV) corresponding to the outer retinal layer (ORL) of the rat retina of FIG. 4A.
Figure 5E:
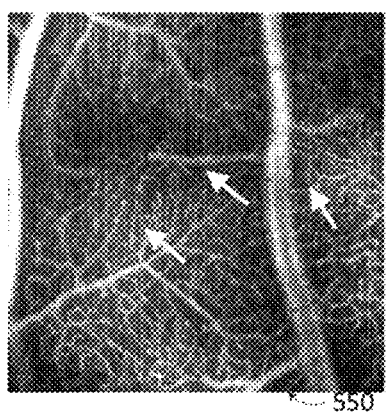
FIG. 5E shows the en face view mean intensity projection of the vasculatures processed with differentiation speckle variance (DSV) corresponding to the middle retinal layer (MRL) of the rat retina of FIG. 4A.
Figure 5F:
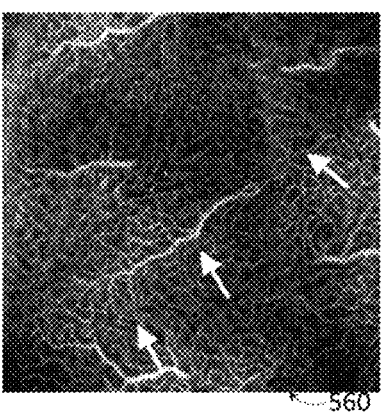
FIG. 5F shows the en face view mean intensity projection of the vasculatures processed with differentiation speckle variance (DSV) corresponding to the inner retinal layer (IRL) of the rat retina of FIG. 4A.

FIGS. 5D-5F depict the en face view mean intensity projections of the vasculatures obtained with the DSV method, corresponding to ORL 540, MRL 550, and IRL 560, respectively. With the suppression of static structure (including the fiber bundles), the vasculature patterns of dynamic blood flow are readily delineated. However, due to the existence of tissue motion, the resulted artifacts may affect the visualization of local perfusion, as indicated by the arrows in 540, 550, and 560. These motion artifacts, as false positive labels of blood vessels, would affect the quantitative results of the vasculature pattern if evaluated with machine recognizable matrices (e.g. vessel area density).

Figure 5G:
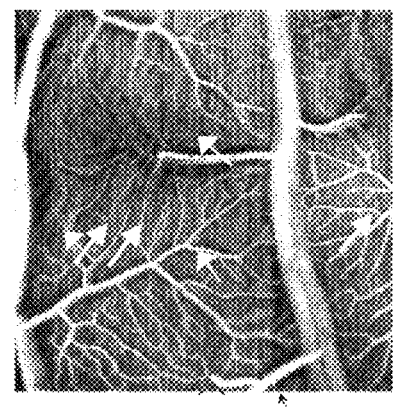
FIG. 5G shows the en face view mean intensity projection of the vasculatures processed with URFA corresponding to the outer retinal layer (ORL) of the rat retina of FIG. 4A.
Figure 5H:
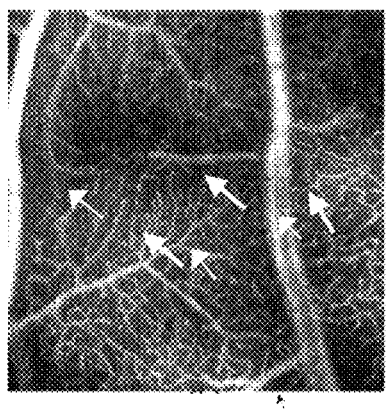
FIG. 5H shows the en face view mean intensity projection of the vasculatures processed with URFA corresponding to the middle retinal layer (MRL) of the rat retina of FIG. 4A.
Figure 5I:
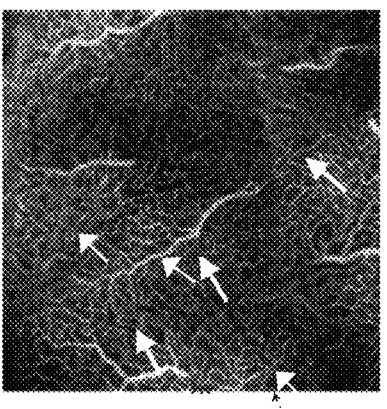
FIG. 5I shows the en face view mean intensity projection of the vasculatures processed with URFA, corresponding to the inner retinal layer (ORL) of the rat retina of FIG. 4A.

In comparison, FIGS. 5G-5I depict the en face view mean intensity projections of the vasculatures obtained from the same dataset with the present URFA, corresponding to ORL 570, MRL 580, and IRL 590, respectively. The motion artifacts are largely reduced with URFA, giving the credits to separately modeling the motion as anisotropic unique variance. The same locations of the artifacts in 540, 550, and 560 are also marked by the arrows in 570, 580, and 590.

One difference between the DSV method and the present URFA method in processing the 3D OCTA volume is that, no thresholding was applied in the URFA method, while a thresholding has to be adopted in the DSV method to further exclude the residual noise for fair comparison of the motion artifacts. This implies that the residual noise, as an independent error variance, may also be reduced in the URFA method.

Figure 6A:
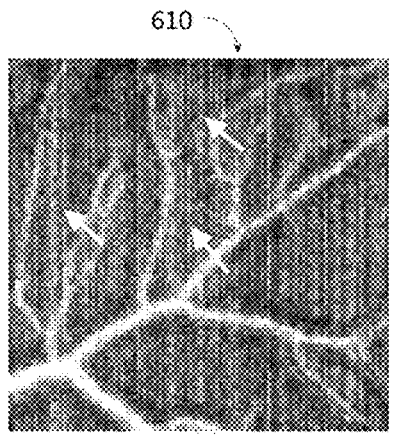
FIG. 6A shows an enlarged mean intensity projection of the vasculatures of FIG. 5D processed with DSV.
Figure 6B:
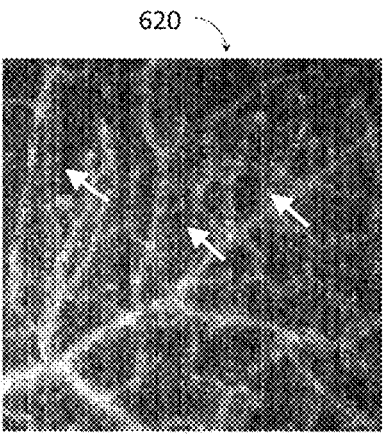
FIG. 6B shows an enlarged mean intensity projection of the vasculatures of FIG. 5E processed with DSV.
Figure 6C:
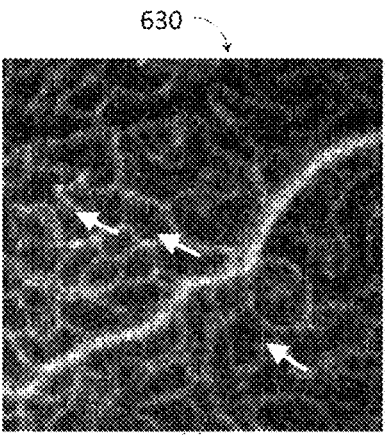
FIG. 6C shows an enlarged mean intensity projection of the vasculatures of FIG. 5F processed with DSV.
Figure 6D:
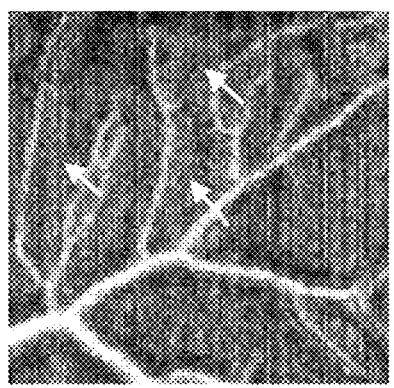
FIG. 6D shows an enlarged mean intensity projection of the vasculatures in FIG. 5G processed with the present URFA.
Figure 6E:
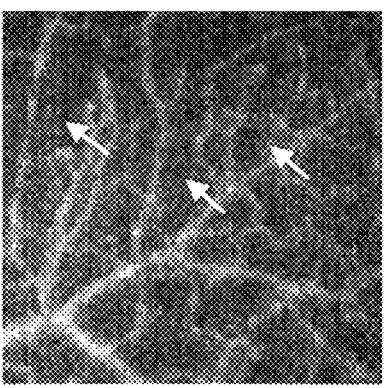
FIG. 6E shows an enlarged mean intensity projection of the vasculatures in FIG. 5H processed with the present URFA.
Figure 6F:
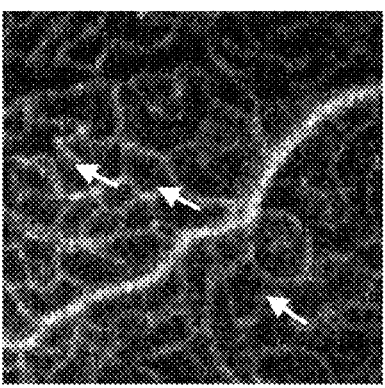
FIG. 6F shows an enlarged mean intensity projection of the vasculatures in FIG. 5I processed with the present URFA.

To better visualize the capillaries, the central 0.3×0.3 mm regions of FIGS. 5D-5I are enlarged as shown in FIGS. 6A-6F. FIGS. 6A-6C show the vasculatures obtained with the DSV method, corresponding to ORL 610, MRL 620, and IRL 630, respectively. FIGS. 6D-6F depict the vasculatures obtained with the present URFA method, corresponding to ORL 640, MRL 650, and IRL 660, respectively. The advantage of the URFA method in the reduction of motion artifacts, as compared with the DSV method, are respectively indicated by arrows in the enlarged images.

Figure 7:
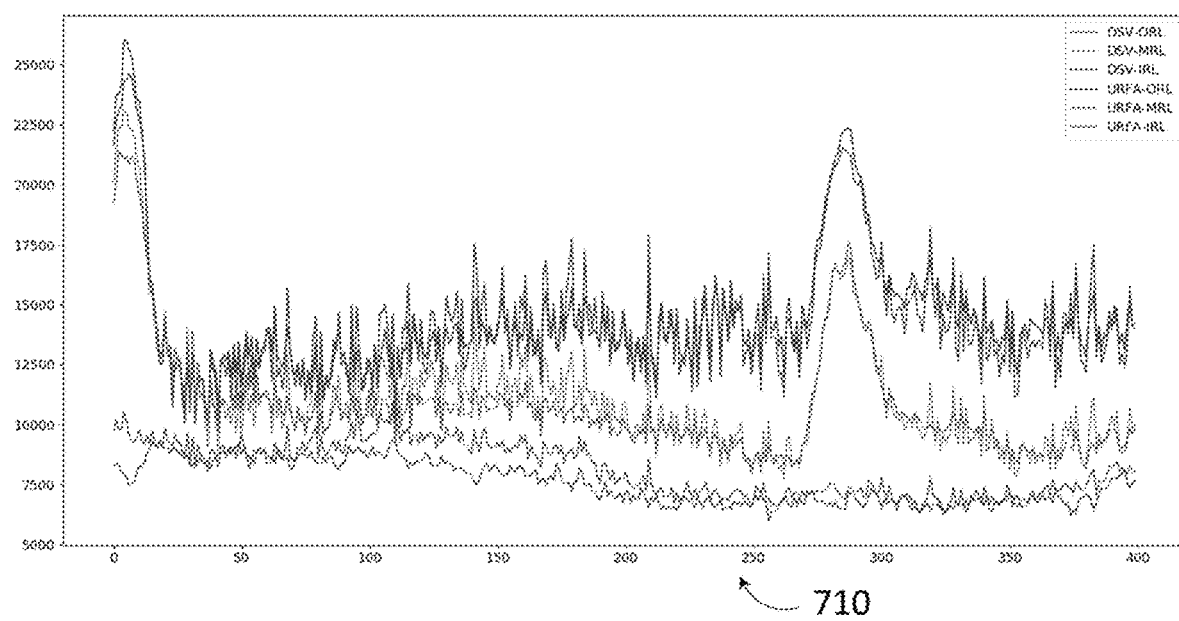
FIG. 7 is a comparison graph illustrating the B-frame averaged intensity profiles of the OCTA images corresponding to FIGS. 5D-5I, respectively.

FIG. 7 is a graph 710 illustrating the frame averaged intensity profiles of the OCTA images in 540, 550, 560 as compared with those in 570, 580, 590, respectively. As the blood vessels are interconnected, if without any motion artifacts, the adjacent B-frames in the OCTA dataset should still possess some level of correlation, leading to a regional smooth change of the frame averaged intensity profile. Therefore, the local variation of the intensity profile in 710 can be used to evaluate how much the motion artifacts affect the angiography results. Practically, the local variation may be calculated as:

$$\text{Local variation} = \sum_{i=1}^{f_N-1} \frac{|I_{i+1} - I_i|}{I_i} \times 100\% \qquad (12)$$

where $f_N$ represents the number of B-frame positions ($f_N$=400 in this example), $|I_{i+1}-I_i|$ represents the absolute value of a subtraction between adjacent pixels in the intensity profile.

As indicated by the local variations in FIG. 8, a significant reduction of motion artifacts is achieved with the present URFA algorithm, as compared with the DSV algorithm. This improvement in performance may be most prominent in the imaging of the MRL. As seen in FIG. 8, the reduction in motion artifacts is at least 10%, and can be a 20% reduction with reductions of 31%, 32% and 47%. That is, as compared to the DSV algorithm, it is believed the present URFA method motion artifacts can be 50% to 70% of the DSV algorithm motion artifacts.

Another application of the present URFA method exists in the visualization of irregular shaped cancer cells and associated vascular system that exhibits significant vessel dilatation, saccular formation, hyper-branching, twisting, and regional angiogenesis. The most common cancer in humans is non-melanoma skin cancer, including basal cell carcinoma and squamous cell carcinoma, with the total number of cases exceeding that of all other cancers combined. In the diagnosis of non-melanoma and melanoma skin cancer, dermatologists may need a 3D high-resolution imaging technique to delineate the boundaries between the cancerous tumor and the benign tissue. In the stage of cancer therapy, instead of directly killing off cancer cells, continuing efforts have been made targeting the tumor vasculature with antiangiogenic agents that may enhance drug delivery, immune cells' infiltration, and immunotherapy efficacy. Finally, the effectiveness of the therapy is monitored and evaluated based on the responses of the cancer cells. Therefore, joint non-invasive and high-resolution 3D imaging of cells and vessels is highly demanded throughout the entire procedure of cancer treatment, from diagnosing the diseases, to making therapeutic plans, and to monitoring the skin responses to medical interventions.

Gabor-domain optical coherence microscopy (GD-OCM) can achieve sub-cellular level 3D resolution, breaking the depth-invariant lateral resolution limit of conventional OCT systems. By using a GD-OCM system with a 2 μm resolution in both lateral and axial directions, in vivo volumetric imaging of epidermal cellular structures of human finger skin can be achieved, in which three different types of cells in *stratum granulosum*, *stratum spinosum*, and *stratum basale* layers are differentiated according to their locations and morphological features (e.g., sizes). GD-OCM can be used in cellular imaging of skin tissue in multiple anatomic locations, including nailfold, forearm, nose, ear, cheek, to name a few. Additionally, GD-OCM can be applied to investigate abnormal skin affected by basal cell carcinoma or squamous cell carcinoma, revealing key characteristic features of cancerous skin such as disrupted skin layers, clusters of dark nested tumor cells, and massive irregularity, which proves its high potential in clinical settings.

Figure 9:
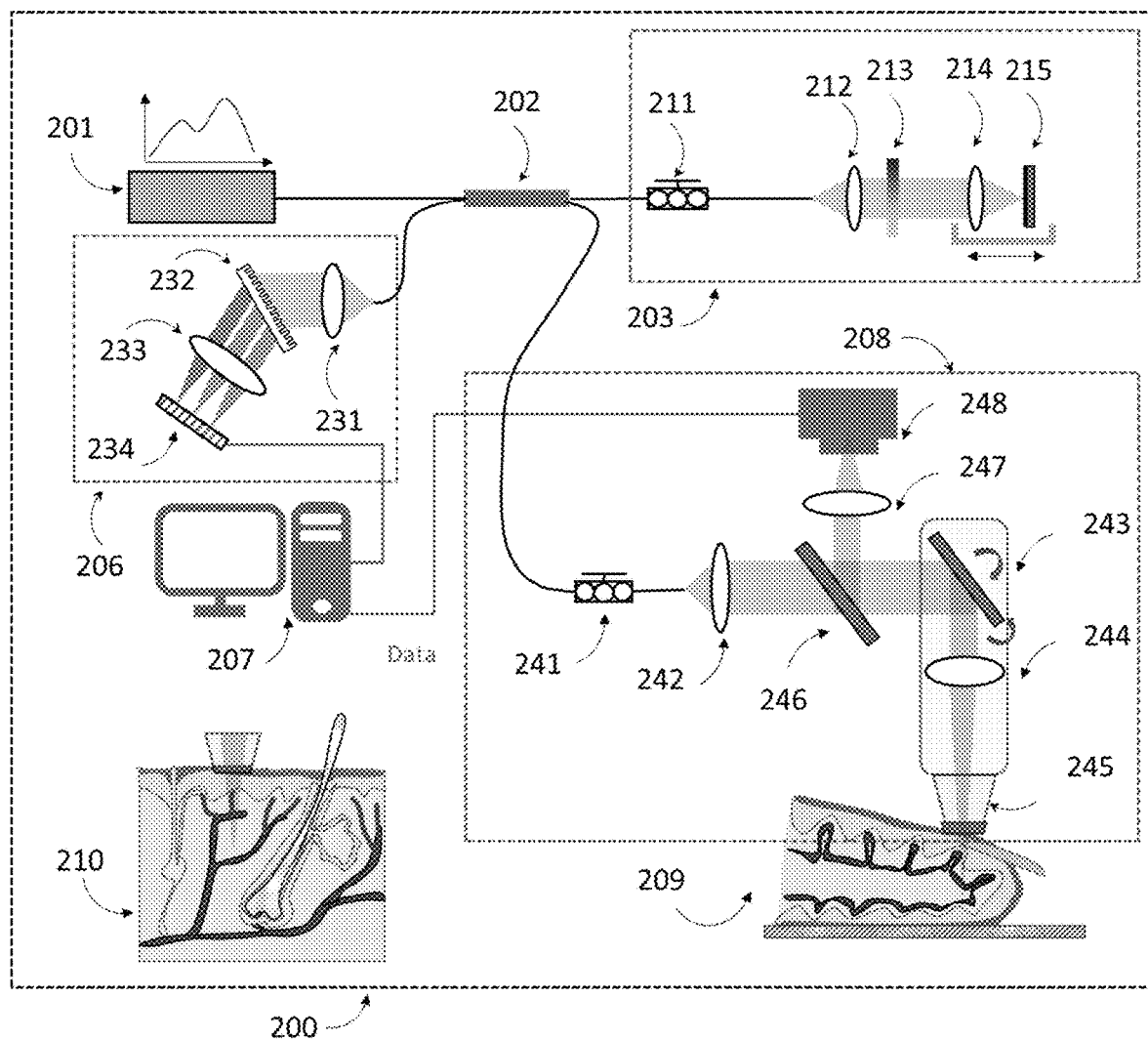
FIG. 9 is a schematic of an alternative exemplary OCT imaging apparatus for the present system.

In the present disclosure, a GD-OCM system can be employed to image the human nailfold cells and vasculature. The schematic of the system is shown in FIG. 9. Different from the aforementioned OCT setup for retina imaging 201-207, the sample arm 204 is replaced with another configuration 208 for GD-OCM system, and the sample eye 205 is replaced with human nailfold 209. The present sample arm 208 includes a polarization controller 241, a collimator 242, a 2D scanner pair 243, an objective lens 244 incorporating a liquid lens for dynamic refocusing, and a contacting spacer 245. Additionally, a 2D image of the nailfold surface may be captured with a dichroic mirror 246, a zoom lens 247, and an RGB camera 248. In the spectrometer 206, a 2048-pixel line-scan camera 234 is adopted, which is controlled at a line period of 20 μs, in order to collect sufficient backscattering photons from the deeper dermis layer. Although the imaging of cells and vasculature is demonstrated based on the human nailfold tissue 209, the present GD-OCM system and URFA processing algorithm are also applicable to other skin tissue with hair and glands, such as forearm, nose, ear and cheek, as schematically shown in 210, as well as other tissues, such as brain tissue and ocular tissue, in healthy conditions or in abnormal conditions such as dermatitis, melanoma and carcinoma.

In this exemplary configuration, imaging of 3D vasculature of a human nailfold in vivo is provided. The scanning protocol consisted of 2,500 B-frames with 580 A-lines in each B-frame. At one cross-sectional location, the B-frame scanning was repeated 5 times with a frame rate of 50 frames per second and a duty cycle of about 50%, resulting in a total acquisition time of 50 seconds. The MEMS scanning along the fast direction (x-direction) was designed following a quasi-linear forward movement with the linear portion >80%, and a fast fly-back movement with the time corresponding to ⅓ that of the forward movement. The lateral sampling of OCM structure and OCM angiography vasculature were both 580 (x-direction)×500 (y-direction), which covered a field of view of 0.5×0.5 mm. The corresponding sample spaces were equal to or smaller than 1 μm, matching the Nyquist sampling of the adopted GD-OCM system with 2 μm lateral resolution.

For a typical adult human, the respiratory rate is about 14 breaths per minute, and the heart beat rate is about 70 beats per minute. Accordingly, a 3D scanning may be affected 12 times by respiratory motion and 58 times by cardiac motion over the 50 seconds acquisition time, and it may additionally be affected by other uncontrollable and unintended skin movements, ranging from faster jerking tics to longer tremors and seizures.

The repeated B-frames of the nailfold are processed with both the present URFA method and the conventional DSV method for visualization of blood flow, and the repeated B-frames are also averaged to enhance the visualization of tissue structure. The resulted OCM and OCM angiography B-frames are stacked into 3D volumes, which are further sliced and/or averaged as en face view projections.

FIG. 10A depicts a photo of the left ring finger of a male adult 910, in which the nailfold region marked by a black square is imaged by the GD-OCM system. FIG. 10B depicts the 3D visualization of the scanned nailfold tissue 920. By slicing through the epidermis and dermis layers, as denoted by the dashed lines in 920, 3 representative cellular structures 930, 940, 950 are visualized, as shown in FIGS. 10C-10E, with respect to averaging the en face view slices of every 12 μm. The cells in the dermis layer are denoted by the arrows in 930, 940, 950, respectively, which may be fibroblasts of different sizes. As the most common cells in connective tissue, fibroblasts are typically large spindle-shaped cells with oval nuclei. The vertically aligned collagen fibers and the surrounding fibroblasts are most prominently displayed in 950. FIG. 10F depicts the en face view mean intensity projection of the nailfold structure, where the boundary between the nail plate and the nailfold soft tissue is demarcated by a dashed curve. Correspondingly, FIG. 10G depicts the en face view mean intensity projection of the nailfold vasculature obtained with DSV. The hairpin "U"-shape capillary loops are readily delineated, indicating the arteriole end and the venule end of a capillary running parallel to the nailfold surface. However, the motion-induced artifacts, appearing as bright vertical line defects that are representatively marked by 3 arrows, severely undermine the visualization of the capillary loops. Moreover, in the acquisition of each B-frame, the MEMS scanner may slightly oscillate at the end of the forward movement (non-linear portion), resulting in additive noise, as indicated by the arrow cluster in 970 (bottom). In contrast to these, as shown in FIG. 10H, with URFA based OCTA processing, both the vertical line artifacts from tissue motion and the residual noise from MEMS oscillation are minimized, providing significant quality improvement in capillary visualization 980. Following equation (12), the calculated local variation is 22.08% for FIG. 10G and 13.08% for FIG. 10H, indicating that the motion artifacts are largely excluded in the present URFA based micro-circulation image. The number of resolved capillary loops is about 6 within the 0.5 mm nailfold tissue, which agrees well with the reported anatomical findings, i.e., the density of nailfold capillaries is about 9-12 per mm.

Additionally, since the time interval between two consecutive frames is relatively long (20 μs), subcellular dynamics in individual fibroblast cells may be captured by the high-resolution GD-OCM system and resolved by the present URFA algorithm, as indicated by the arrow head in 980. The region by side of the nail-nailfold boundary is largely free of the dynamic signal of subcellular motion, as this region is usually occupied by the cuticle that consists of a thin layer of dead cells.

As is well known, blood vessels and fibroblasts play important roles in the wound healing of skin. During healing of tissue injury, fibroblasts migrate to the site of damage, where they break down the fibrin clot, create new extra cellular matrix and deposit new collagen structures. Meanwhile, new blood vessels formed through the angiogenesis process bring nutrients, immune cells and oxygen to facilitate the healing process. The present method, by integrating GD-OCM system with URFA algorithm, provides an effective way of imaging the capillary as an indicator of nutritional support and the subcellular dynamic as an indicator of cell viability, which would help in understanding the cell metabolism in normal and abnormal conditions. The reduction of motion artifacts for vascular and subcellular imaging in vivo and in situ would further speed up the clinical translation of the present technique from benchmark to bedside.

Three-dimensional (3D) vascular imaging of biological tissue in vivo with high resolution is important for the diagnosis and management of pathological conditions. The present URFA method provides an effective way to map the tissue perfusion with reduced motion artifacts. The present disclosure provides the imaging of label-free endogenous flow of blood cells, which can image the perfusion from repeated scans of the tissue structure. Thus, the present disclosure provides the ability to image the vasculature of in vivo and in vitro tissue, wherein the tissue includes animal and human tissue including adult, adolescent or infant tissue.

The present system leverages OCM and particularly GD-OCM, to achieve sub-cellular level 3D resolution and cubic millimeter range field-of-view, thus surpassing the resolution limit of conventional OCT systems. Additionally, the present URFA algorithm provides method of reducing motion-induced artifacts for high-resolution OCT angiography by which cerebrovascular perfusion, ocular microcirculation, skin microcirculation, and the related disease progressions can be more clearly imaged. That is, the present method can reduce noise attributable to bulk motion including bulk tissue motion without significant sacrifice in the flow signal or static tissue signal in the common variances. In light of the resolution of the present method, the common variances can include at least one of cellular motion and sub-cellular motion, which can then be imaged in the display image.

This disclosure has been described in detail with particular reference to an embodiment, but it will be understood that variations and modifications can be affected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method of imaging tissue to reduce motion artifacts, the method comprising:
   (a) modeling, with a data processing engine, an optical coherence tomography dataset having a plurality of depth encoded profile of tissue reflections along an optical axis as Gaussian latent variables to differentiate common variances comprising static tissue structure and dynamic blood flow and unique variances comprising tissue motion in the optical coherence tomography dataset to generate a model;
   (b) iteratively, with the data processing engine, (i) fitting the model through an exploratory factor analysis to derive corresponding dynamic factors and static factors and (ii) calculating an objective function as a summation of log-likelihood probabilities of the common variances and the unique variances until a calculated improvement of fitting is less than a predetermined threshold or a maximum number of iterations have been performed to generate a fitted model;

(c) applying, with the data processing engine, the fitted model to the optical coherence tomography dataset to reduce unique variances and isolate the dynamic factors from the static factors in the common variances to reduce motion artifacts and produce a plurality of images; and (d) generating a display image by summing absolute values of a frame averaged intensity profile of the plurality of images.

2. The method of claim 1, wherein the optical coherence tomography dataset includes at least one of two dimensional and three dimensional scans of a target tissue.

3. The method of claim 1, further comprising subdividing the common variances into multiple factors.

4. The method of claim 1, wherein the optical coherence tomography dataset includes data corresponding to a dynamic blood flow and further comprising resolving the common variances in the optical coherence tomography dataset by summing the values of images corresponding to a predetermined number of factors.

5. The method of claim 1, wherein applying the fitted model includes performing a maximization of the summated log-likelihood probabilities to reduce the unique variances, and an expectation step of an expectation-maximization algorithm to isolate the dynamic factors from the static factors in the common variances.

6. The method of claim 1, wherein the plurality of images corresponds to the dynamic factors.

7. The method of claim 1, wherein the dataset includes data corresponding to in vivo tissue and steps (a) through (c) isolate the unique variance due to tissue motion to reduce the motion artifacts in the resulting images.

8. The method of claim 1, wherein the display image is a cross-sectional OCT angiography image.

9. The method of claim 1, wherein the common variances include at least one of cellular motion and sub-cellular motion.

10. The method of claim 1, wherein the unique variances are at least one of a bulk motion and a bulk tissue motion.

11. The method of claim 1, wherein the common variances include blood flow.

12. A method of in vivo imaging to reduce motion artifacts, the method comprising:

(a) scanning, by an optical coherence tomography imager, a tissue sample to generate an optical coherence tomography dataset comprising spectral interference data corresponding to the scanning of a portion of the tissue sample;

(b) modeling, with a data processing engine, the optical coherence tomography dataset as Gaussian latent variables to differentiate static tissue structure and dynamic blood flow from tissue motion;

(c) iteratively maximizing, with the data processing engine, a combined log-likelihood probability of the modeled static tissue structure, the modeled dynamic blood, and the tissue motion by exploratory factor analysis to derive corresponding factors and exclude at least a portion of the tissue motion;

(d) separating, with the data processing engine, the modeled dynamic blood from the modeled tissue structure to generate a plurality of images; and (e) generating a display image of blood flow in the tissue by summing absolute values of a frame averaged intensity profile of images corresponding to predetermined orders of factors.

13. The method of claim 12, wherein separating the modeled dynamic blood from the modeled tissue structure includes integrating factors representing a level of correlation.

14. The method of claim 12, wherein the level of correlation of the modeled dynamic blood is less than the level of correlation of the static tissue structure.

15. The method of claim 12, wherein the display image is a cross-sectional OCT angiography image.

16. An apparatus for reducing motion artifacts in vivo imaging, the apparatus comprising:

(a) an optical coherence tomography imager configured to scan in vivo tissue and generate an optical coherence tomography dataset, the optical coherence tomography dataset comprising data corresponding to spectral interference data from the optical coherence tomography imager scan of the in vivo tissue, the optical coherence tomography imager including a data processing engine, the data processing engine configured to generate an image of the in vivo tissue by (a) iteratively (i) fitting, by the data processing engine, the optical coherence tomography dataset as a model of Gaussian latent variables differentiating common variances comprising static tissue structure and dynamic blood flow and unique variances comprising tissue motion in the optical coherence tomography dataset through an exploratory factor analysis to derive corresponding factors and (ii) calculating, by the data processing engine, an objective function as a summation of log-likelihood probabilities of the common variances and the unique variances until a calculated improvement of fitting is less than a predetermined threshold or a maximum number of iterations have been performed to generate a fitted model to reduce motion artifacts; (b) performing, by the data processing engine, an expectation step of the fitted model to generate a plurality of images; and (c) generating a display image having reduced motion artifacts, by summing absolute values of a frame averaged intensity profile of the plurality of images.

17. The method of claim 16, further comprising separating the common variances of the dynamic blood from the static tissue structure by integrating factors representing a level of correlation.

18. The method of claim 16, wherein the level of correlation of the modeled dynamic blood is less than the level of correlation of the static tissue structure.

19. The method of claim 16, wherein the display image is a cross-sectional OCT angiography image.

20. The method of claim 16, wherein the common variance includes at least one of cellular motion and sub-cellular motion.

21. The method of claim 16, wherein the unique variance is at least one of a bulk motion and a bulk tissue motion.

22. The method of claim 16, wherein the common variance includes blood flow.

* * * * *